United States Patent [19]

Schutz et al.

[11] Patent Number: 5,087,781

[45] Date of Patent: Feb. 11, 1992

[54] METHOD OF MAKING MESITYLENE

[75] Inventors: Alain A. Schutz, Penn Township, Westmoreland County; Leonard A. Cullo, Greensburg, both of Pa.

[73] Assignee: Aristech Chemical Corporation, Pittsburgh, Pa.

[21] Appl. No.: 710,843

[22] Filed: Jun. 6, 1991

[51] Int. Cl.$^5$ .................. B01J 23/00; B01J 23/16; C07C 15/02; C07C 1/20

[52] U.S. Cl. .................. 585/409; 585/400; 585/469; 502/246; 502/353

[58] Field of Search .............. 585/400, 409; 502/353, 502/246

[56] References Cited

U.S. PATENT DOCUMENTS

| | | | |
|---|---|---|---|
| 1,977,178 | 2/1933 | Heidelberg | 585/409 |
| 2,419,142 | 4/1947 | Ipatieff et al. | 260/668 |
| 2,425,096 | 8/1947 | Ipatieff et al. | 260/668 |
| 2,833,833 | 5/1958 | Schmerling | 260/668 |
| 2,917,561 | 12/1959 | Eby | 260/668 |
| 3,201,485 | 8/1965 | Kovach | 260/668 |
| 3,267,165 | 8/1966 | Kimble et al. | 260/668 |
| 3,301,912 | 1/1967 | Hwang et al. | 260/668 |
| 3,413,372 | 11/1968 | Hurley, Jr. | 260/668 |
| 3,946,079 | 3/1976 | Mizutani et al. | 260/593 R |

*Primary Examiner*—Asok Pal
*Assistant Examiner*—P. Achutamurthy
*Attorney, Agent, or Firm*—William L. Krayer

[57] ABSTRACT

Mesitylene (1,3,5 trimethylbenzene) is made by passing acetone in the vapor phase over a niobium catalyst. The catalyst is preferably made by impregnating a silica support with 2% niobium by weight and calcining for about 18 hours at about 550° C. 70% selectivity is obtained at 60-80% by weight conversion.

5 Claims, No Drawings

METHOD OF MAKING MESITYLENE

TECHNICAL FIELD

The present invention relates to a process for the preparation of mesitylene (1,3,5 trimethylbenzene) by vapor phase reaction of acetone in the presence of a niobium supported catalyst.

BACKGROUND OF THE INVENTION

Several methods for making mesitylene from acetone are known and include, for example:

liquid phase condensation in the presence of strong acids, e.g. sulfuric acid and phosphoric acid as described in U.S. Pat. No. 3,267,165 (1966).

vapor phase condensation with tantalum containing catalysts as described in U.S. Pat. No. 2,917,561 (1959).

vapor phase condensation using as catalyst the phosphates of the metals of group IV of the periodic system of elements, e.g. titanium, zirconium, hafnium and tin as described in U.S. Pat. No. 3,946,079 (1976).

vapor phase reaction in the presence of molecular hydrogen and a catalyst selected from the group consisting of alumina containing catalytic amounts of chromia and boria and silica-alumina containing catalytic amounts of chromia and zinc oxide as described in U.S. Pat. No. 3,201,485 (1965).

vapor phase reaction using catalysts containing molybdenum as described in U.S. Pat. No. 3,301,912 (1967) or tungsten as described in U.S. Pat. No. 2,425,096.

Most of the common acidic materials tested (zeolites, silico-alumina and modified alumina) deactivate very fast and produce large amounts of isobutene and acetic acid from the cracking reaction of mesityl oxide or diacetonealcohol.

SUMMARY OF THE INVENTION

We have found that mesitylene can be produced from acetone by a vapor phase reaction over a niobium supported catalyst with high selectivity. The catalyst is preferably made by impregnating a silica support with an ethanolic solution of $NbCl_5$ or an aqueous solution of Nb oxalate in order to deposit 2% Nb by weight and by calcining the final solid at 550° C. for 18 hours. At 300° C., the condensation of acetone produces mainly mesitylene (70% selectivity) at high conversion (60–80% wt).

1,3,5 trimethylbenzene or mesitylene may be made from acetone, which is a plentiful material. Mesitylene's symmetry and high reactivity (electrophilic substitutions are activated by the methyl groups) lead to the possibility of synthesizing specific derivatives such as polymethylaromatics, trimesic acid, hindered diamines, and other as described in U.S. Pat. Nos. 4,254,196, 3,925,488, 4,340,767, 3,928,433, and JP 7,807,795, JP 7,397,830, and JP 7,868,760.

Compared to its actual industrial production from reformates, a process using acetone would have the advantage of not producing pseudocumene (1,2,4 isomer), 1,2,3 trimethylbenzene and transalkylation products (xylenes and tetramethylbenzene). For example, when pseudocumene is contacted with a strong Friedel-Crafts catalysts (KOCH process, 127° C.), the reactor effluent contains mainly 21% xylenes, 44% trimethylbenzenes and 29% tetramethylbenzenes. The isomeric composition of the 44% trimethylbenzenes is 29.5% mesitylene, 66% pseudocumene and 4.5% 1,2,3 trimethylbenzene which have to be separated by superfractionation.

A possible mechanism for its formation from acetone is shown below and involves the condesation of three molecules via aldol reaction and the formation of three molecules of water.

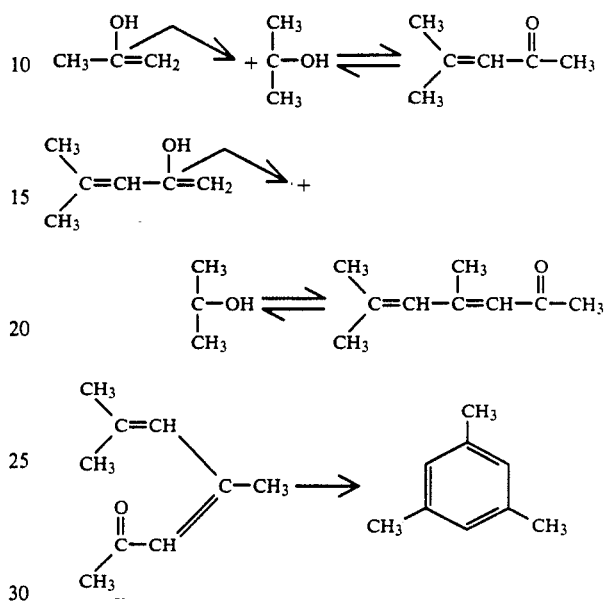

As the acid strength required for aldol condensation is much lower than for isomerisation of alkylaromatics, weak acidic catalysts should produce mesitylene selectively.

DETAILED DESCRIPTION OF THE INVENTION

Some sreening reactions were carried out based on U.S. Pat. No. 2,917,561, Dec. 1959, Esso Research and Engineering Company, which used tantalum oxide supported on silica. Niobium, tungsten and molybdenum oxides supported on silica were also compared. The results demonstrated that mesitylene can be synthesized with high selectivity (up to 72 wt%) at high conversion (40–70%). Differences between the various catalysts were found in selectivities to acetic acid and isobutene which can be directly correlated to electronegativities or acid strengths of the elements. Tantalum oxide, the least acidic material, produced the minimum cracked products but formed the largest quantities of compounds identified as tetramethylcyclohexadienes. These have boiling points close to that of mesitylene and it is expected that their separation from mesitylene will be difficult; therefore, they have to be minimized or selectively hydrogenated in order to obtain high purity mesitylene. It is noteworthy that the isomers of mesitylene are essentially not formed which gives to this process a significant advantage compared to alkylation and isomerization of substituted aromatics.

A preliminary reaction test has been done with a $\frac{3}{4}"$ reactor (tantalum oxide on silica) and has reproduced previous results obtained on a microreactor. Additionally, by running at different temperatures we found that mesitylene selectivity increases with conversion and temperature. Also, at high temperature, fewer tetramethylcyclohexadienes are formed while acetic acid and isobutene increase slightly. Finally, the slow and steady deactivation of the catalyst (from 70 to 60% conversion after one week) shows that a potential process should have the capability of regenerating the catalyst frequently. For this purpose, a fluidized bed reactor may be preferred.

For all these materials the by-products were mainly isobutene, acetic acid (cracking of mesityl oxide and intermediates) and a series of products (molecular weight 96, 136, 176 and 216) perhaps formed from the reaction of acetone with isobutene or from the cracking of higher condensates. Also, an aromatic compound identified as 3,5-dimethyl-1-(2-butenyl)benzene is formed from the condensation of four molecules of acetone. The overall reaction selectivity is shown in the following structural formulas:

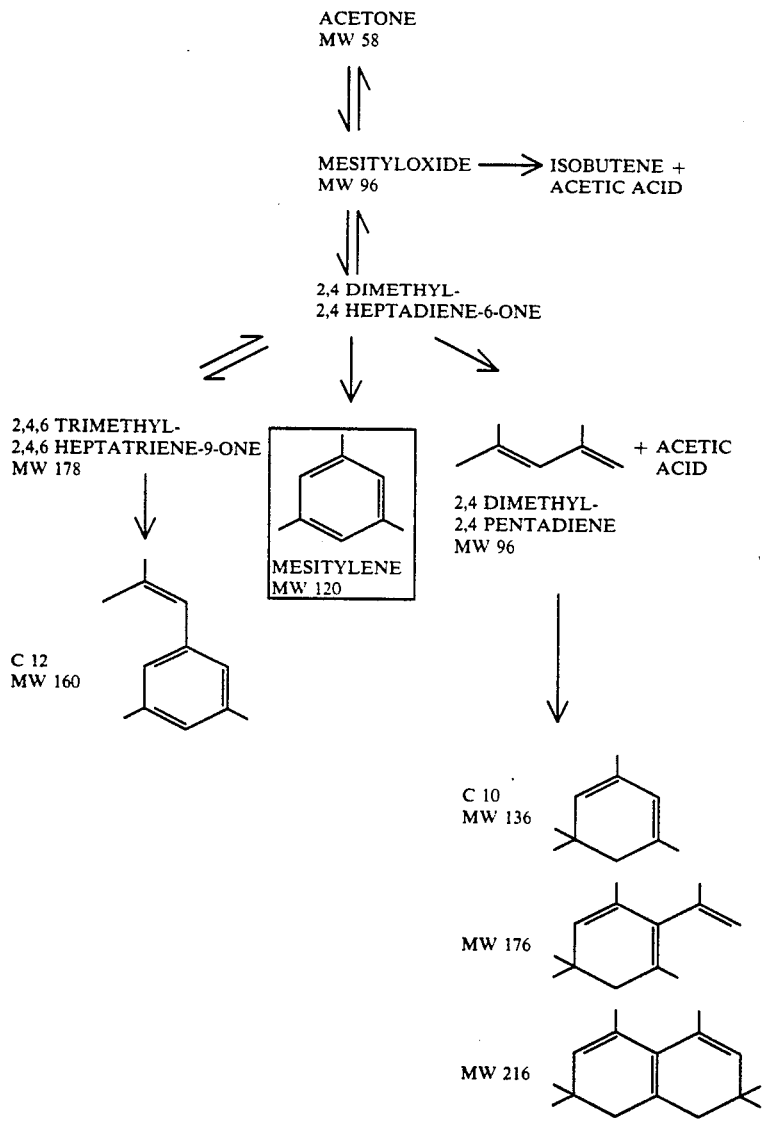

ACETONE MW 58

MESITYLOXIDE MW 96 → ISOBUTENE + ACETIC ACID 2,4 DIMETHYL-2,4 HEPTADIENE-6-ONE 2,4,6 TRIMETHYL-2,4,6 HEPTATRIENE-9-ONE MW 178

MESITYLENE MW 120

2,4 DIMETHYL-2,4 PENTADIENE MW 96 + ACETIC ACID

C 12 MW 160

C 10 MW 136

MW 176

MW 216

Results obtained with the sreening reactor are presented in the following Table I. All catalysts have been prepared by impregnating a powder silica support with an ethanolic solution of chloride salts of Ta, Nb, W and Mo in order to obtain 2 wt% of metal. After drying, the catalysts have been calcined under air for 18 hours at 550° C.

TABLE I

| | G.C. Area percent. | | | | | |
|---|---|---|---|---|---|---|
| Acetone | Isobutene | Acetic Acid | Mesityl oxide | C10 | Mesitylene | C12 |
| Tantalum catalyst, reaction at 300° C. | | | | | | |
| 17 | 4.5 | 4 | 1.5 | 3.8 | 48.1 | 6.6 |
| 22 | 3.5 | 1.5 | 3.5 | 4.6 | 47.4 | 8.0 |
| Niobium catalyst, reaction at 300° C. | | | | | | |
| 40 | 8.0 | 1 | 0.6 | <1 | 39.8 | 3.5 |
| Niobium catalyst, reaction at 350° C. | | | | | | |
| 18 | 7.0 | 1 | 0.5 | <1 | 58.1 | 4.7 |
| 16 | 5.0 | 1 | 0.6 | <1 | 62.1 | 5.4 |
| Niobium catalyst, reaction at 400° C. | | | | | | |
| 7 | 5.0 | 2 | 0.5 | <1 | 65.5 | 4.5 |
| Tungsten catalyst, reaction at 300° C. | | | | | | |
| 52 | 20 | 7 | 3.2 | 0 | 15.0 | 0.4 |
| 44 | 19 | 4 | 2.9 | 0 | 23.0 | 2.5 |
| Molybdenum catalyst, reaction at 300° C. | | | | | | |
| 21 | 13 | 2 | 5.7 | 0.1 | 41.0 | 4.7 |
| 50 | 1.2 | <1 | 7.2 | 0.1 | 24.0 | 5.4 |

C10 = Tetramethylcyclohexadienes M.W. 136 (three isomers)
C12 = Benzene-1-(2-butenyl)-3,5-dimethyl M.W. 160

All catalysts gave essentially the same products, without isophorone, but with different selectivities. The formation of by-products, e.g. isobutene and C10 as shown in Table I are minimum for the niobium supported catalyst. It shows that isobutene and acetic acid selectivities increase with the acidity of the oxides or the electronegativity of the elements while C10 amounts decrease. Consequently, mesitylene selectivity is optimum when both kinds of by-products are minimized, e.g. with niobium oxide which gives 73 wt% mesitylene selectivity at 350° C.

Results of a reaction test using a ¾" reactor is shown in the following Table II. The catalyst was prepared by impregnating 1/16" extruded silica support (PQ Corporation CS-1010-E) with an ethanolic solution of TaCl5 in order to have 3% Ta. The catalyst was calcined at 550° C. for 18 hours. The reactor was loaded with 35 g (65 cm$^3$) of material and 50 ml/hour of acetone was passing downflow in the reactor at 300° C. inlet for the first 50 hours and at 400° C. for the next 96 hours.

TABLE II

| Time on stream | G.C. Area percent of organic phase | | | | |
|---|---|---|---|---|---|
| | Acetone | Mesityl oxide | C10 | Mesitylene | C12 |
| 300° C. inlet | | | | | |
| 16 h | 30 | 1.8 | 2.3 | 44 | 6.6 |
| 24 h | 36 | 2.7 | 1.9 | 39 | 5.9 |
| 40 h | 37 | 2.9 | 1.9 | 38 | 6.0 |
| 50 h | 40 | 3.6 | 1.8 | 36 | 5.8 |
| 400° C. inlet, same catalyst charge | | | | | |
| 4 h | 17 | 1.1 | 1.1 | 59.1 | 6.9 |
| 20 h | 20 | 1.1 | 1.0 | 57.0 | 6.1 |
| 28 h | 21 | 1.3 | 1.0 | 56.0 | 6.7 |
| 44 h | 23 | 1.7 | 1.0 | 54.0 | 6.7 |
| 52 h | 23 | 1.5 | 1.0 | 55.7 | 6.3 |
| 68 h | 28 | 2.5 | 1.0 | 48.0 | 6.3 |
| 76 h | 31 | 2.5 | 1.0 | 47.3 | 6.3 |
| 92 h | 33 | 3.5 | 0.9 | 45.0 | 6.0 |

Calculated mesitylene selectivities were 61% and 70% for reaction temperatures of 300° C. and 400° C., respectively. Also, the undesirable C10s decrease by a factor 2 when the temperature is increased from 300° C. to 400° C. During the second period, the catalyst deactivated from 70% to 60% conversion after 92 hours of reaction.

Other reaction tests were done on niobium supported catalysts to study the effect of niobium oxide loading. All catalysts were prepared by impregnating a silica support with aqueous solutions of Nb oxalate in order to deposit 1, 2, 5 and 8 wt% niobium oxide. Also, a pure niobium oxide catalyst was tested for comparison. The results are shown in Table III. The data show that there is an optimum in niobium loading which gives the highest conversion and mesitylene selectivity.

TABLE III

| wt % Nb$_2$O$_5$ | Acetone conversion wt % | Mesitylene selectivity wt % |
|---|---|---|
| 1 | 12 | 23 |
| 2 | 30 | 65 |
| 5 | 18 | 40 |
| 8 | 18 | 30 |
| 100 | 6 | 20 |

We claim:

1. Method of making mesitylene comprising passing acetone over a niobium supported catalyst at a temperature of about 250° C. to about 500° C.

2. Method of claim 1 wherein the catalyst support is silica.

3. Method of claim 1 wherein the catalyst is made by impregnating a silica support with niobium chloride.

4. Method of claim 1 wherein the catalyst is made by impregnating a silica suport with niobium oxalate.

5. Method of claim 1 wherein the catalyst comprises about 0.5% to about 3% by weight niobium impregnated on a silica support.

* * * * *